United States Patent
Sughrue et al.

(10) Patent No.: US 11,699,232 B2
(45) Date of Patent: Jul. 11, 2023

(54) BRAIN HUB EXPLORER

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU); Xinling Jiang, Willoughby (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/464,649

(22) Filed: Sep. 1, 2021

(65) Prior Publication Data

US 2023/0065967 A1    Mar. 2, 2023

(51) Int. Cl.
*G06T 7/00* (2017.01)
*G06T 7/32* (2017.01)

(52) U.S. Cl.
CPC ........... *G06T 7/0012* (2013.01); *G06T 7/32* (2017.01); *G06T 2207/20092* (2013.01); *G06T 2207/30016* (2013.01)

(58) Field of Classification Search
CPC ............ G06T 7/0012; G06T 7/32; G06T 2207/20092; G06T 2207/30016
See application file for complete search history.

(56) References Cited

U.S. PATENT DOCUMENTS 10,537,277 B2 *   1/2020   Wu ................... G01R 33/4812
10,849,563 B2    12/2020   Sackellares et al.
2013/0035922 A1*  2/2013   Martens ................ G16H 50/50
                                                          703/11
2013/0113816 A1*  5/2013   Sudarsky .............. G06T 11/206
                                                          345/589
2014/0222738 A1*  8/2014   Joyce .................... G16H 50/50
                                                          706/47

(Continued)

FOREIGN PATENT DOCUMENTS

EP          3865061        8/2021

OTHER PUBLICATIONS

International Search Report and Written Opinion in International Appln. No. PCT/AU2022/050518, dated Sep. 6, 2022, 10 pages.

*Primary Examiner* — Vu Le
*Assistant Examiner* — Winta Gebreslassie
(74) *Attorney, Agent, or Firm* — Fish & Richardson P.C.

(57) ABSTRACT

Disclosed herein are systems and methods for providing interactive graphical user interfaces (GUIs) for users, such as medical professionals, to glean insight about connectivity data associated with a particular brain. A method can include overlaying nodes representing locations of parcels of a patient's brain on a representation of a brain and displaying the representation of the brain with the overlaid nodes in a GUI. Nodes having connectivity above a first threshold can be represented in a first indicia and nodes having connectivity below a second threshold can be represented in a second indicia. The method can include receiving user input and taking an action based on the user input. The user input can include selecting an area of the representation of the brain for excision. Taking an action based on the input can include calculating an impact of excising the area of the brain on the particular patient.

20 Claims, 9 Drawing Sheets

(56) References Cited

U.S. PATENT DOCUMENTS

| | | |
|---|---|---|
| 2017/0052241 A1 | 2/2017 | Cetingul et al. |
| 2018/0368720 A1 | 12/2018 | Lee et al. |
| 2019/0053726 A1* | 2/2019 | Geva .................... A61B 5/7246 |
| 2019/0187233 A1* | 6/2019 | Topgaard ............... G01N 24/08 |
| 2019/0206057 A1* | 7/2019 | Cranmer .............. A61B 5/0263 |
| 2020/0352443 A1 | 11/2020 | Fox |
| 2020/0352542 A1* | 11/2020 | Errico .................. A61B 8/0891 |
| 2021/0170180 A1* | 6/2021 | Dosenbach .......... A61B 5/0042 |

* cited by examiner

BRAIN HUB EXPLORER

TECHNICAL FIELD

The subject matter described herein generally relates to processing images of brains and displaying information about the brains using an interactive brain navigation system and interface.

BACKGROUND

Medical imaging includes techniques and processes for creating visual representations of an interior of a body for clinical analysis and medical intervention, as well as visual representation of physiology of some organs or tissues. Medical imaging can reveal internal structures hidden by skin and bones, and can be used to diagnose and treat various diseases. Medical imaging also can establish a database of normal anatomy and physiology to make it possible to identify abnormalities amongst cohorts. Some medical imaging can also provide insights into functional activity and structural connections of a brain.

SUMMARY

This document generally describes technologies for processing medical images of brains and/or displaying the processed images in a user-interactive brain navigation system (e.g., interface). The disclosed technology can be used by clinicians and other medical professionals to glean insight about structures and connections in a subject's brain (e.g., patient, human, animal, or other specimen). Based on such insights, the clinicians and other medical professionals can perform improved and more informed diagnoses, treatments, operations, and/or research than with existing systems.

For example, brain surgery can involve making cuts into the brain. In order to perform brain surgery, one can use a standard brain atlas containing a standard parcel or parcellation scheme, regardless of the specifics of the particular brain being considered. The term "parcel" or "parcellation" refers to the process of delineating regions of the brain that have similar properties between individuals, such as functional activity, cytoarchitecture, and structural connectivity. In this nomenclature, a "parcellation" is a region of the brain (e.g., cortex) that can be shown to have similar properties across individuals, even if the exact boundaries may differ. Parcellating a brain is a useful mechanism for analyzing neuroimaging data as it reduces complexity of the brain's activity to a finite number of domains, which can be assumed to play somewhat uniform functions.

Lack of precise parcellation information relating to a particular brain in question can, when surgery is performed, lead to collateral damage to brain functions, such as cognition. One can align an atlas (e.g., a set of three-dimensional (3D) points or voxels assigning voxels identity in a standard coordinate space to various parcellations) to the brain after warping it into a standard coordinate space, such as the Montreal Neurologic Institute (MNI) space. Pure anatomic-based techniques of atlasing can fail when applied to patients with structurally abnormal brains, such as those with brain tumors, stroke, hydrocephalus, traumatic brain injury and atrophy. For these and other reasons, there is a need to be able to map and visualize functional areas in individuals (e.g., in individuals with varying brains) in a way that addresses these issues, as it would make a number of valuable analytics possible to improve outcomes.

Brain graphs can be a useful way to display connectivity data amongst portions of the brain. However, brain graphs can become cluttered, thereby making it more challenging to analyze relationships between points of connectivity and to link connectivity data to actual anatomic structures of other clinical workflows. The disclosed technology, therefore, provides unique GUIs that can display relevant graph data of a brain over a glass brain. The relevant graph data can be displayed in such a way that allows medical professionals and other users to view individual nodes (e.g., hubs, parcellations) and edges (e.g., fibers) of a particular patient's brain. The medical professional can then use such GUIs to more clearly identify and analyze structures in the brain from other aspects of a connectomic interface.

For example, one way to analyze a brain is by using constructs such as hubs and parcellations. Sometimes, a medical procedure may require cutting into, puncturing, or otherwise excising one or more hubs or portions thereof. Medical professionals must be well informed about connectivity data associated with the particular patient's brain since a wrong cut, puncture, incision, and/or excision can cause negative, long term effects for the patient. Such negative effects may apply to some patients but not others, especially since each patient has different connectivity data associated with their particular brain. Thus, the disclosed technology provides GUIs that can be used by the medical professional to identify hubs and connectivity data associated with the particular patient and to make more informed decisions about what steps to take during a medical procedure. Identifying which hubs of the brain can be impacted for the particular patient can be a challenging process with existing graph theory techniques.

The disclosed technology provides a way for the medical professional to view, conceptualize, and analyze, for each patient brain, connectivity data associated with that particular brain. Using the disclosed technology, the medical professional can selectively view different nodes, edges, hubs, parcellations, or other portions of the brain. The medical professional can simulate one or more steps that may be taken during a medical procedure, such as excising a volume of a hub or removing particular nodes in the brain, in order to receive information about how the patient would respond as a result of the medical procedure (e.g., develop negative long-term effects such as depression). A series of visualizations presented to the medical professional can allow the medical professional to interact with the particular brain in such a way that improves the medical professional's ability to diagnose, treat, analyze, or otherwise study the particular patient's brain.

One or more embodiments described herein include a method that includes overlaying nodes representing locations of parcels of a patient's brain on a representation of a brain and displaying the representation of the brain with the overlaid nodes in a graphical user interface (GUI). Nodes having a connectivity above a first threshold can be represented in a first indicia and nodes having a connectivity below a second threshold can be represented in a second indicia. The method can also include receiving user input, and taking an action based on the user input.

The embodiments described herein can optionally include one or more of the following features. For example, the connectivity of the nodes can be a number of connections between the nodes. The connectivity of the nodes can also be a correlation of activity of bold signals. In some implementations, the connectivity of the nodes can be a number of connections between the nodes and a correlation of activity in bold signals.

As another example, the connectivity of the nodes can be based at least in part on diffusion weighted imaging (DWI) data indicating tracks that connect to the parcels of the patient's brain. The connectivity of the nodes can also be based at least in part on blood oxygen consumption of the parcels of the patient's brain.

As yet another example, the user input can include selection of an area or volume of the representation of the brain for excision. Moreover, taking an action based on the user input can include calculating an impact of excising the area or volume of the representation of the brain. The impact of excising the area or volume of the representation of the brain can include interferences on cognitive functionality of the patient's brain. In some implementations, taking an action based on the user input can include removing one or more of the overlaid nodes in the excised area or volume of the representation of the brain. In yet some implementations, taking an action based on the user input further can include removing additional nodes of the overlaid nodes. The additional nodes can be connected to the one or more of the overlaid nodes that are in the excised area or volume of the representation of the brain.

As another example, the user input can include hovering over one or more of the overlaid nodes, and taking an action based on the user input can include displaying information about the one or more of the overlaid nodes over a portion of the GUI.

In some implementations, one or more of the parcels of the patient's brain can include hubs. The method can also include retrieving, from a data store, image data of the patient's brain. The parcels of the patient's brain could have been annotated and labeled in the image data. In some implementations, the first indicia can be a first color and the second indicia can be a second color. Sometimes, the user input can include selection of one of the overlaid nodes, and taking an action based on the user input can include displaying information about the selected one of the overlaid nodes in a second GUI.

In some implementations, the method can also include connecting high connectivity nodes and low connectivity nodes by edges. The edges can represent fibers. The method can also include displaying, in the GUI, a graph with the edges of correlation. In some implementations, the nodes in the first indicia can have high centrality and the nodes in the second indicia can have low centrality.

One or more embodiments described herein can include a system having at least one programmable processor, and a machine-readable medium storing instructions that, when executed by the at least one programmable processor, cause the at least one programmable processor to perform operations. The operations can include overlaying nodes representing locations of parcels of a patient's brain on a representation of a brain, displaying the representation of the brain with the overlaid nodes in a graphical user interface (GUI), receiving user input, and taking an action based on the user input. Nodes having a connectivity above a first threshold can be depicted in a first indicia and nodes having a connectivity below a second threshold can be depicted in a second indicia.

The subject matter described herein provides numerous advantages. For example, the disclosed technology can provide medical professionals with an interface that allows for gleaning insights about a brain. Present imaging systems can be cumbersome to use and operate, and typically can produce outputs that lack clinical usefulness. The disclosed technology, on the other hand, processes images of the brain and outputs them in an interactive, user-friendly graphical user interface (GUI) of a brain navigation system. The medical professional can then interact with portions of the particular brain in question using the GUI. As a result, the medical professional can glean more insight about the parcellations of the particular brain, which can be used to determine appropriate diagnoses, treatments, surgical procedures, and other research or clinical purposes that are specific to the particular brain in question.

The disclosed technology can also provide for a simple way to link outputs of a graph measure to an actionable item, such as an anatomic structure. Brain graphs can be difficult to study in a meaningful way. Thus, the disclosed technology transforms brain graphs into interactive, user-friendly depictions in 3D space that make it easier for a user, such as the medical professional, to glean insight about different aspects of a particular brain. The disclosed technology can, for example, depict connectivity between different nodes and edges in the particular brain. Connectivity data can be visually represented in a variety of ways to further assist the user's understanding and analysis of connectivity in the particular brain. Colors, for example, can be used, where some colors, such as red, can depict higher connectivity and other colors, such as blue, can depict lower connectivity. The GUIs of the disclosed technology can include user-friendly functionality that provides ease of use to the user. For example, the user can hover over nodes and/or edges in order to view additional information about such features of the patient's brain. The user can also simply click on or select nodes, edges, or portions of the glass representation of the brain in order to simulate removal of such selected features during a medical procedure. As a result, the user can quickly and easily view repercussions and/or effects of performing such actions during a medical procedure before performing the medical procedure. This can be advantageous for the user to tailor how they perform the medical procedure and/or what actions they take to diagnose and/or treat the patient.

As another example, the disclosed technology provides for improving an ability of the medical professional to assess a condition of a particular patient's brain. Each patient can have different connectivity data associated with their brain, thereby making certain treatment and/or medical procedures effective for some patients while not effective for others. The disclosed technology provides for visualizing a particular patient's connectivity data on a glass representation of a brain so that the medical professional can more easily and accurately analyze the particular patient's brain and make more informed decisions about what diagnosis, treatment, and/or medical procedures to take for that particular patient.

The details of one or more variations of the subject matter described herein are set forth in the accompanying drawings and the description below. Other features and advantages of the subject matter described herein will be apparent from the description, drawings, and claims.

BRIEF DESCRIPTION OF DRAWINGS

Like reference symbols in various drawings indicate like elements.

DETAILED DESCRIPTION

Figure 1:
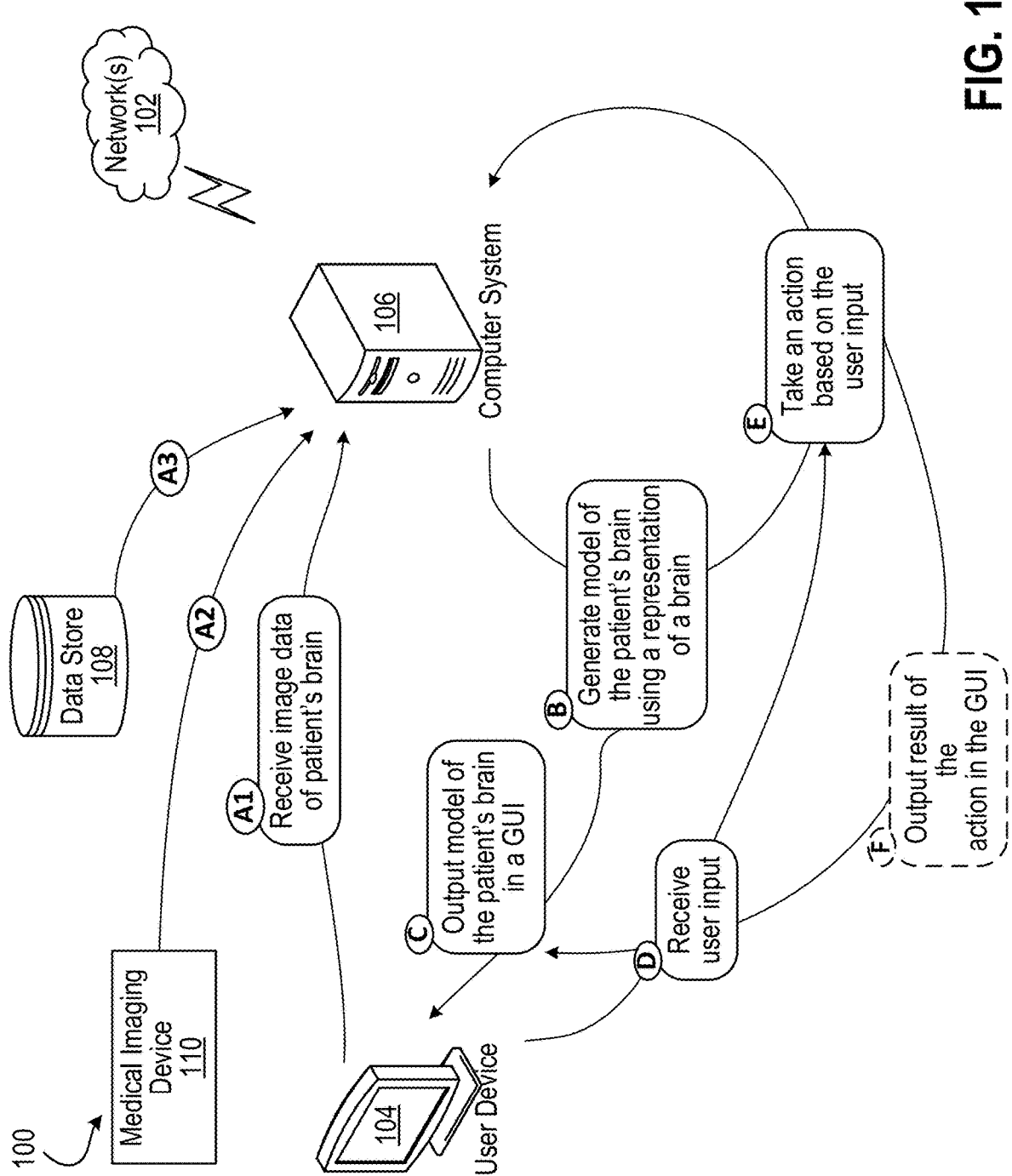
FIG. 1 is a conceptual diagram illustrating a computing environment for generating a GUI representation of a particular brain.

This document generally relates to providing interactive GUIs for users, such as medical professionals, to glean insight about connectivity data associated with a particular brain. Using the GUIs, for example, a medical professional can more accurately tailor diagnosis, treatment, and/or procedures for a particular patient and their particular condition. Using the disclosed technology, imaging data of a brain can, for example, be overlaid on a glass brain (e.g., a 3-dimensional (3D) representation of a brain). This modelled version of the brain can be outputted in a GUI or other user interface display at a user device. Although this disclosure is described from a perspective of a medical professional, the disclosed technologies can be used by any other type of user.

The medical professional can interact with the modelled version of the brain in order to analyze the particular patient's connectivity data and to make more informed decisions about how to address the particular patient's brain condition. The medical professional can hover over nodes and/or edges of the modelled brain to view information about those areas/features of interest. For example, names and/or weights can be outputted and displayed in the GUI when the medical professional hovers over a particular node or edge. Sometimes, the medical professional can also highlight or select one or more nodes having high and/or low graph measures (e.g., centrality, participation, modularity measures, etc.) to view additional information about such features of interest. The medical professional can adjust or switch between different views of the patient's brain. For example, the medical professional can select options to view only portions (e.g., hubs, parcellations, left side, right side, etc.) of the patient's brain. The medical professional can select options to view nodes and edges in different colors, where the colors identify different levels of connectivity.

The medical professional can click on nodes and/or edges in order to view the brain in an atlas form with a selected parcellation and/or parcellation/tract combination loaded therein. The medical professional can more easily identify which parcellations belong, or not, to a community of parcellations, which can show plasticity. As described throughout, selecting nodes and/or edges can also cause the disclosed technology to simulate effects of removing the selected features from the particular patient's brain, as if the features were being removed during an actual medical procedure. Thus, the modelled brain can be reconfigured without the removed features and results that this removal would have on other nodes, edges, and/or parcellations in the particular brain can be presented to the medical professional. The medical professional can use this information to determine whether removing such nodes and/or edges during the actual medical procedure would have long term effects on the particular patient (e.g., depression or other cognitive impairments).

Referring to the figures, FIG. 1 is a conceptual diagram illustrating a computing environment 100 for generating a GUI representation of a particular brain. The computing environment 100 can include a user device 104, a computer system 106, a data store 108, and a medical imaging device 110, which can communicate (e.g., wired and/or wirelessly) via network(s) 102.

The user device 104 can be used by a medical professional, such as a clinician, surgeon, doctor, nurse, researcher, or other professional. The user device 104 and technologies described herein can be used by any other user. The user device 104 can be any one of a computer, laptop, tablet, mobile device, mobile phone, and/or smartphone. Sometimes, the user device 104 can be integrated into or otherwise part of one or more other devices in a medical setting, such as the medical imaging device 110 and/or the computer system 106. The medical professional can use the user device 104 to view information about a patient's brain. For example, using the disclosed technology, the medical professional can view, at the user device 104, 3D representations of a particular patient's brain and make determinations about what diagnosis, treatment, and/or surgical procedures to perform. The medical professional can also view other/ additional information about the particular patient at the user device 104 to make more informed decisions with regards to the particular patient's diagnosis, treatment, surgery, or other medical or research purposes. Thus, the user device 104 can provide hardware that can support the GUIs, software, and applications described herein, such as a singular and interactive brain navigation system that makes it easier and more intuitive for the medical professionals to make medical and research determinations.

The computer system 106 can be a remote computing system, a cloud-based system or service, and/or integrated with or otherwise part of one or more devices in a medical setting (e.g., such as the user device 104 and/or the medical imaging device 110). The computer system 106 can be a computer, processor, a network of computers, a server, and/or a network of servers. Sometimes, each medical setting (e.g. a hospital) can have one or more computer systems 106. Sometimes, the computer system 106 can be used across multiple medical settings (e.g., multiple hospitals). The computer system 106 can be configured to generate interactive representations of patients' brains based off image data of the brains. The computer system 106 can also generate GUIs to display the interactive representations of the brains at the user device 104.

Sometimes, the computer system 106 can clean the image data by removing personally identifying information (e.g., protected health information (PHI)) from that data. Cleaning the image data can be beneficial to preserve patient privacy, especially if the interactive representations of patients' brains are used for medical research, clinical studies, or otherwise are stored in the data store 108 for future retrieval and use. Removing personally identifying information can also be advantageous if the computer system 106 is remote from the user device 104 and the interactive representations of the brain are generated at the computer system 106 that is outside a secure hospital infrastructure or other network where the image data may be generated and/or the interactive representations of the brain may be outputted. In other words, removing personally identifying information can be advantageous to preserve patient privacy when patient data is communicated between different networks and/or infrastructure.

The data store 108 can be a remote data store, cloud-based, or integrated into or otherwise part of one or more other components in the medical setting (e.g., such as the user device 104 and/or the computer system 106). The data store 108 can store different types of information, including but not limited to image data of patient brains (e.g., from the medical imaging device 110), cleaned image data (e.g., from the computer system 106), 3D representations of patient brains or other interactive representations of patient brains (e.g., from the computer system 106), connectivity data associated with patient brains, determinations, actions, or other user input taken by the medical professional (e.g., at the user device 104), patient information or records, or other relevant information that can be used in a medical setting.

The medical imaging device 110 can be any type of device and/or system that is used in the medical setting to capture image data of patient brains. The medical imaging device 110 can capture image data that includes but is not limited to x-rays, computed tomography (CT) scans, magnetic resonance imaging (MRIs), and/or ultrasound. One or more other types of image data can also be captured by the medical imaging device 110. The computer system 106 can be configured to receive any type of image data of a patient's brain and glean connectivity data about the brain from that image data to map the data onto a user-friendly interactive representation of a brain.

Still referring to FIG. 1, the computer system 106 can receive image data of a patient's brain from one or more of the user device 104 (step A1), the medical imaging device 110 (step A2), and the data store 108 (step A3). Sometimes, for example, when the user device 104 is part of the medical imaging device 110, the computer system can receive the image data captured by the medical imaging device 110 from only one device (e.g., the medical imaging device 110 or the user device 104). The image data can be captured by the medical imaging device 110 then sent directly, in real-time, to the computer system 106 (step A2) for real-time processing. Sometimes, the image data can be captured by the medical imaging device 110, then initially reviewed by the medical professional at the user device 104. Accordingly, the user device 104 can transmit the image data to the computer system 106 (step A1).

In some implementations, image data can be captured of multiple different brains by multiple different medical imaging devices 110. The image data can be stored in the data store 108 for future processing and analysis. The computer system 106 can then retrieve a batch or batches of the image data from the data store 108 (step A3) and process the image data in batch. Processing in batch can be advantageous to use fewer computational resources and reduce network bandwidth.

Once the computer system 106 receives the image data (steps A1-A3), the computer system can generate a model of the brain using a representation of a brain (step B). For example, the computer system 106 can map or model the patient's brain from the image data onto a 3D representation of a brain. The 3D representation can be a generic brain in 3-dimensional or other multi-dimensional space. The 3D representation can be a glass brain. Mapping the patient's brain onto the glass brain can be advantageous to provide vantage points of different structures, parcellations, and connectivity in the particular patient's brain. A medical professional can more easily analyze the particular patient's brain via the 3D representation of the brain rather than through the raw image data captured by the medical imaging device 110. As a result, the medical professional can generate more informed decisions and determinations with regards to the particular patient's diagnosis, treatment, surgery, condition, or other medical or research purposes.

Once the patient's brain is modeled using the representation of the brain (step B), the computer system 106 can output the model of the patient's brain in a GUI at the user device 104 (step C). For example, the computer system 106 can generate the GUI that displays the model of the patient's brain, then transmit the GUI to the user device 104 to be outputted. The model can represent the patient's brain overlaid on the glass brain. Sometimes, instead of outputting the model at the user device 104 (step C), the computer system 106 can store the model of the patient's brain in the data store 108. The model of the patient's brain can then be accessed/retrieved at a later time and presented to the medical professional or other user at the user device 104.

As mentioned throughout, when the model of the patient's brain is outputted at the user device 104, the GUI can allow the medical professional to take numerous actions in response to reviewing the model of the patient's brain. For example, the medical professional can determine what type of diagnosis, treatment, or surgical procedures to take with regards to this particular patient. The medical professional can also interact with the model of the patient's brain through use-selectable options and features in the GUI that is outputted at the user device 104. The medical professional can change views of the model of the patient's brain (e.g., rotate around the model, view only a left or right side of the patient's brain, etc.), select portions of the patient's brain from the model (e.g., select a particular lobe, node, parcellation, etc.), view other information about the patient (e.g., health records, prior medical visits, etc.), and simulate surgical procedures that can impact different parcellations or portions of the patient's brain (e.g., slicing a node or nodes that are connected to other nodes in the patient's brain). The medical professional can provide input to the user device 104, for example, via an input device, and the input can indicate the medical professional's interaction(s) with the model of the patient's brain. This input can then be received by the computer system 106 (step D).

The computer system 106 can take an action based on the received user input (step E). For example, if the medical professional changes or selects a different view of the model of the patient's brain, then the computer system 106 can generate an updated GUI display of the patient's brain that only includes the selected view. This updated GUI display can be outputted at the user device (step F). As another example, the medical professional can remove one or more nodes from the model of the patient's brain. The computer system 106 can receive this input (step D), simulate removal of the user-selected nodes (step E), then output results of removing such nodes from the brain at the user device 104 (step F). The medical professional can review the outputted results and take further actions in response. Further actions can include decisions about what nodes the medical professional should remove during the actual medical procedure and/or how to proceed with diagnosis, treatment, and/or the medical procedure.

Sometimes, the computer system 106 can take an action based on the user input (step E) that does not also include outputting a result of the action at the user device 104 (step F). For example, the medical professional can input notes about what actions the medical professional intends to take during a medical procedure, a diagnosis for the particular patient, and/or treatment for the patient. The computer system 106 can receive this input and store it in the data store 108 but may not output results from storing this input. This input can then be retrieved from the data store 108 and provided to one or more other devices (e.g., a report can be generated that indicates the patient's diagnosis and treatment). The report can then be provided to a device of the patient. The report can also be transmitted to devices of other medical professionals, such as those in a hospital infrastructure/network). The computer system 106 can take one or more other actions based on the user input (step E) and optionally output results of the action(s) at the user device 104 (step F).

Figure 2:
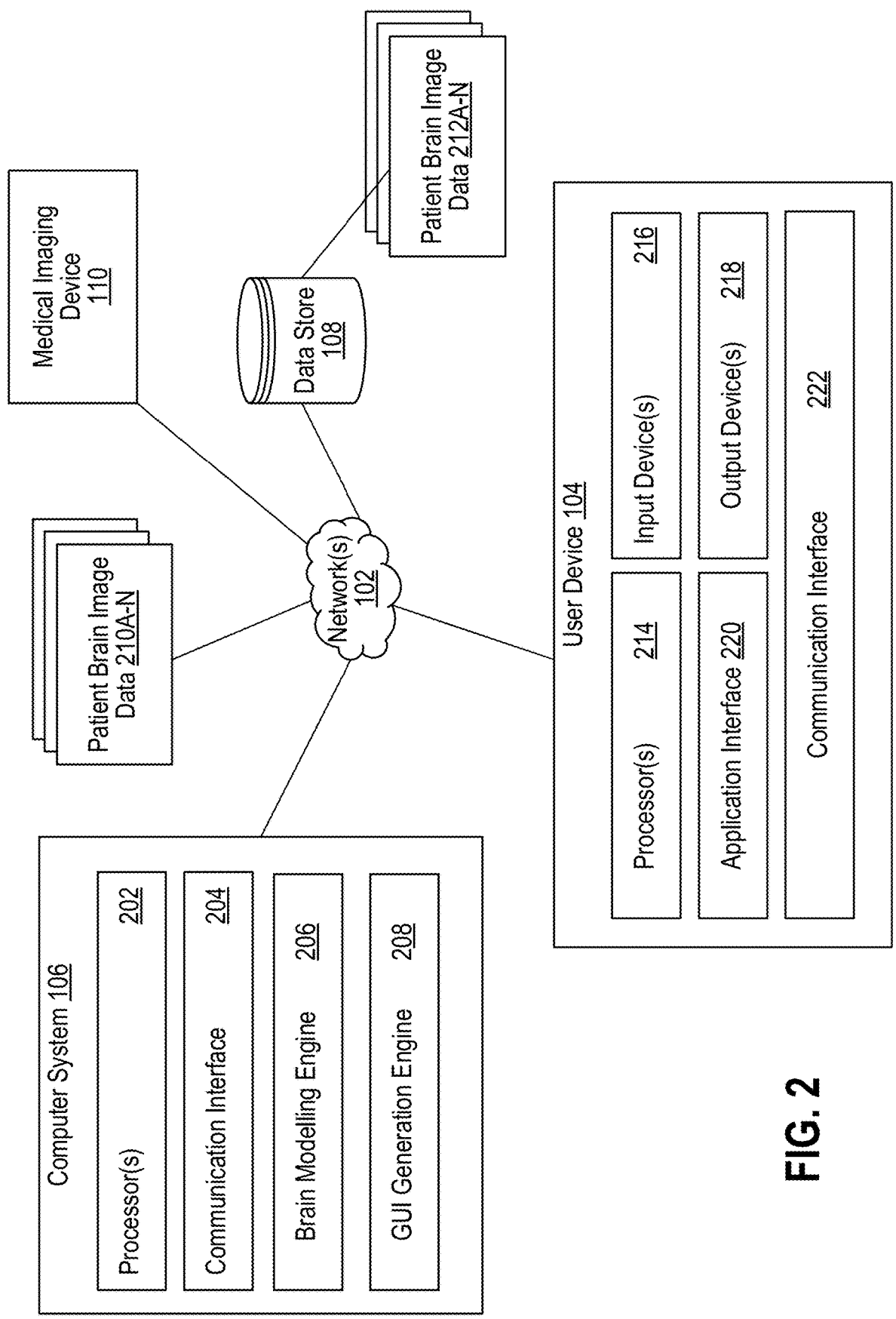
FIG. 2 illustrates components in a computing landscape that can be used to generate the GUI representation of the particular brain.

FIG. 2 illustrates components in a computing landscape that can be used to generate the GUI representation of the particular brain. As described above, the user device 104, computer system 106, data store 108, and medical imaging device 110 can communicate via the network(s) 102. One or more of the components 104, 106, 108, and 110 can also be integrated into a same computing system, network of devices, server, cloud-based service, etc. The network(s) 102 may be a wide-area network (WAN), such as the Internet, a cellular telecommunications network, or a private WAN. Connection via the network(s) 102 can include a traditional dial-up modem, a high-capacity (e.g., cable) connection such as a broadband modem, and/or a wireless modem.

The computer system 106 can include processor(s) 202, communication interface 204, brain modelling engine 206, and GUI generation engine 208. The processor(s) 202 can be configured to perform one or more operations described herein. Although not depicted, the computer system 106 can also include at least one memory unit, which may have semiconductor random access memory (RAM) and semiconductor read only memory (ROM).

One or more of the techniques and processes described herein can be implemented as software application programs executable by the processor(s) 202 in the computer system 106. Moreover, one or more of the techniques and processes described herein can be executed in browsers at remote terminals, systems, or devices (e.g., the user device 104 and/or another computer system), thereby enabling a user of the remote terminals, systems, or devices to access the software application programs that are executing on the computer system 106. For example, steps for any of the techniques and processes described herein can be effected by instructions in the software application programs that are carried out within the computer system 106. Software instructions may be formed as one or more code modules (e.g., using PYTHON or equivalent language modules installed on the computer system 106 and/or the remote terminals, systems, or devices), each for performing one or more particular tasks. The software instructions can also be divided into separate parts. For example, a first part and the corresponding code module(s) can perform the techniques and processes described herein and a second part and the corresponding code module(s) can manage a user interface (e.g., the GUIs described herein) between the first part and the medical professional at the user device 104.

Moreover, the software may be stored in a non-transitory, tangible, computer readable medium, including storage devices described throughout this disclosure. The software can be loaded into the computer system 106 from the computer readable medium, and then executed by the computer system 106. A computer readable medium having such software or computer program recorded on the computer readable medium can be a computer program product. Examples of transitory or non-tangible computer readable transmission media that may also participate in the provision of software, application programs, instructions and/or data include radio or infra-red transmission channels as well as a network connection to another computer or networked device, and the Internet or Intranets, including e-mail transmissions and information recorded on Web sites and the like.

Still referring to the computer system 106, the brain modelling engine 206 can be configured to map a patient's brain onto a representation of a brain (e.g., refer to step B in FIG. 1). For example, the brain modelling engine 206 can receive patient brain image data 210A-N, which can be used to generate a model of the patient's brain. The patient brain image data 210A-N can be received from the medical imaging device 110. The patient brain image data 210A-N can also be received from the user device 104. In some implementations, as described in reference to FIG. 1, the computer system 106 can retrieve patient brain image data 212A-N from the data store 108. The patient brain image data 212A-N can then be used by the brain modelling engine 206 to model the patient's brain.

Sometimes, modelling the brain can include identifying connectivity data for the particular brain. Modelling the brain can then include mapping the connectivity data over the representation of a generic brain. In yet some implementations, modelling the patient's brain can include identifying hubs, parcellations, deep nodes, lateral nodes, and other portions of the patient's brain that can be mapped onto the representation of the generic brain. Moreover, the brain modelling engine 206 can be configured to identify personally identifying information in the image data of the brain and extract that information before mapping the patient's brain onto the representation of the generic brain. The brain modelling engine 206 can use one or more machine learning models to accurately map the particular patient's brain data onto a representation of the generic brain.

In some implementations, for example, Digital Imaging and Communications in Medicine (DICOM) images of a particular brain to be parcellated can be processed by the brain modelling engine 206. DICOM is an international standard for transmitting, storing, retrieving, processing and/or displaying medical imaging information. A registration function for the particular brain can be determined in a Montreal Neurological Institute (MNI) space (a common coordinate space) described by a set of standard brain data image sets, a registered atlas from a human connectome project can be determined, and diffusion tractography of the DICOM images can be performed to determine a set of whole brain tractography images of the particular brain (in neuroscience, tractography can be thought of as a 3D modelling technique used to represent white matter tracts visually). For each voxel in a particular parcellation in the registered atlas, voxel level tractography vectors showing connectivity of the voxel with voxels in other parcellations can be determined, the voxel can be classified based on the probability of the voxel being part of the particular parcellation, and determining of the voxel level tractography vectors and the classifying of the voxels for all parcellations of the HCP-MMP1 Atlas can be repeated to form a personalised brain atlas (PBs Atlas) containing an adjusted parcellation scheme reflecting the particular brain.

The GUI generation engine 208 can be configured to generate GUI displays of the modelled brain. The GUI generation engine 208 can receive the modelled brain from the brain modelling engine 206 and generate an appropriate GUI for displaying the modelled brain to the medical professional (e.g., refer to FIG. 3). The GUI generation engine 208 can also transmit the generated GUI(s) to the user device 104 to be outputted/presented to the medical professional.

Moreover, whenever user input is received from the user device 104 that includes performing some action in response to the outputted model of the brain, the input can be received by the computer system 106. The brain modelling engine 206 can take some action (e.g., refer to step E in FIG. 1) in response to receiving the user input (e.g., refer to step D in FIG. 1). That action can include, for example, simulating removal of one or more nodes in the patient's brain. The GUI generation engine 208 can generate updated GUI displays based on the actions taken by the brain modelling engine 206 (e.g., refer to step F in FIG. 1). The GUI generation engine 208 can then transmit the updated GUI displays to the user device 104 to be outputted to the medical professional.

Sometimes, one or more of the components of the computer system 106, such as the brain modelling engine 206 and the GUI generation engine 208 can be part of one or more different systems. For example, the brain modelling engine 206 can be part of a software application program that can be loaded and/or executed at another device, such as the user device 104 and/or the medical imaging device 106. As another example, the GUI generation engine 208 can be part of a software application program that is executed at the user device 104 and the brain modelling engine 206 can be executed at the computer system 106 or another remote computing system, server, or cloud-based server or system.

The user device 104 can include processor(s) 214, input device(s) 216, output device(s) 218, application interface 220, and communication interface 222. The processor(s) 214 can be configured to perform one or more operations described herein. Although not depicted, the user device 104 can also include at least one memory unit, which may have semiconductor random access memory (RAM) and semiconductor read only memory (ROM).

The input device(s) 216 and output device(s) 218 can include one or more of an audio-video interface that couples to a video display, speakers, and/or a microphone, keyboard, mouse, scanner, camera, touch screen display, other display screen(s) (e.g., LCDs), joystick, and/or other human interface device. The input device(s) 216 can be configured to receive user input from the medical professional or other user. The output device(s) 218 can be configured to output the model of the patient's brain and/or actions taken by the computer system 106 in response to the user input. The output device(s) 218 can present a variety of GUI displays and information to the medical professional, where such displays and information are generated by the computer system 106. The output device(s) 218 can also output information that is received or otherwise generated by the medical imaging device 110.

The application interface 220 can be executable software or another program that is deployed at the user device 104. The GUIs generated by the computer system 106 can be displayed or otherwise outputted via the application interface 220. In some implementations, the application interface 220 can be executed at a browser of the user device 104. The medical professional can then access and view the GUIs via the Internet or other connection. Sometimes, the application interface 220 can be executed as a software module/program/product at the user device 104. The application interface 220 can provide the interactive GUIs to the medical professional and receive input from the medical professional (e.g., refer to FIG. 3).

The communication interfaces 204 and 222 can be configured to provide communication between and amongst the components described herein. For example, a modem can be integrated therein.

Figure 3:
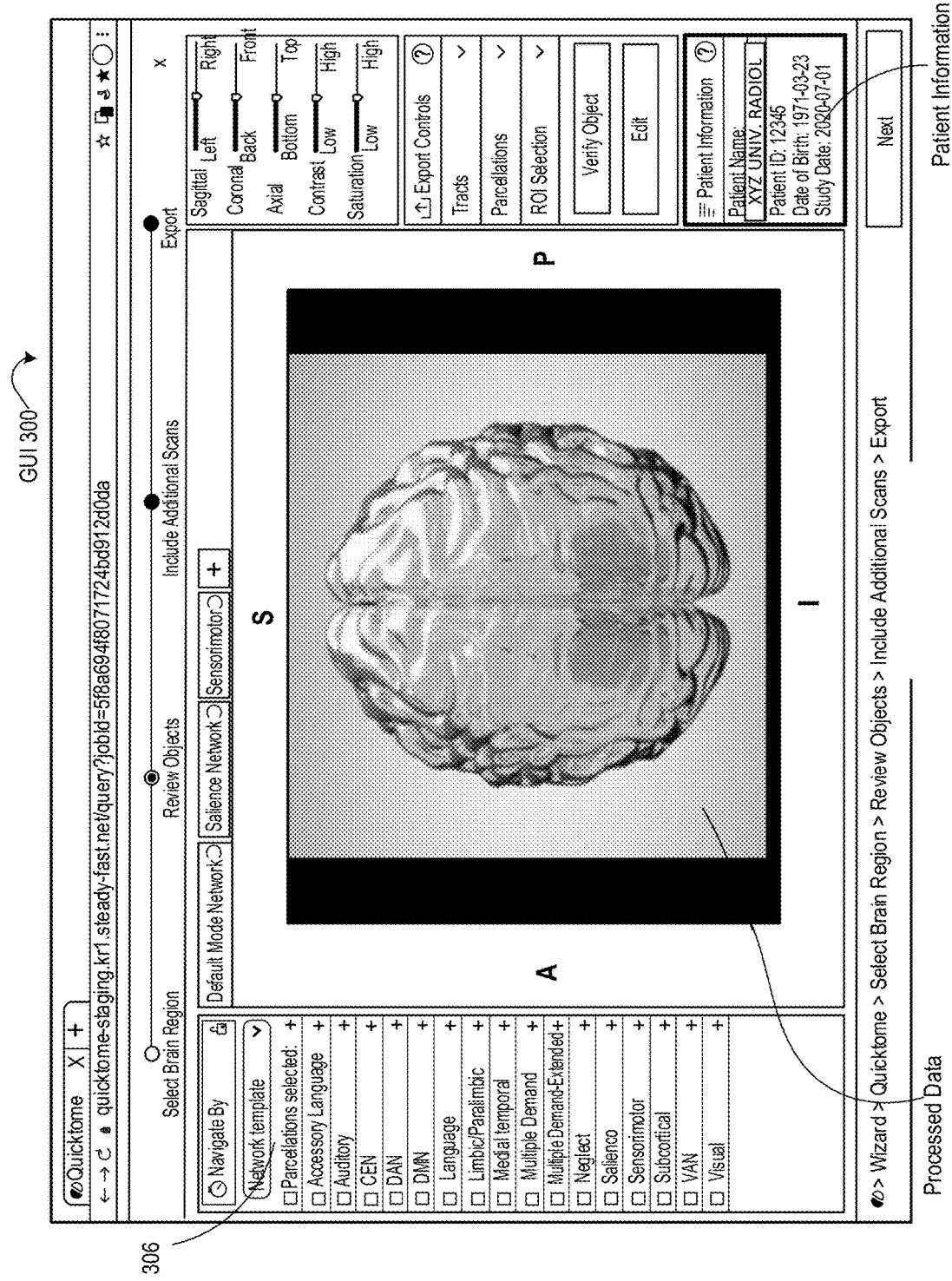
FIG. 3 illustrates a user-interactive GUI display of the particular brain.

FIG. 3 illustrates a user-interactive GUI 300 of the particular brain. The GUI 300 can be outputted at the user device 104 described herein. The GUI 300 outputs processed medical imaging data that is received of the particular brain. For example, the GUI 300 can include processed data 302, patient information 304, and selectable options 306. The processed data 302 can include the particular brain as it is modeled on a representation of a brain. For example, the processed data 302 can include a 3D representation of the particular brain, such as the particular brain overlaying a glass brain. The processed data 302 also may not include other information that can appear in imaging data, such as patient information or other PHI. The PHI that corresponds to the processed data 302 can optionally be outputted in the patient information 304.

The GUI 300 can provide a brain navigation system that is configured to display visual representations of an interior of the particular brain for clinical analysis and medical intervention, as well as visual representation of physiology of specific portions or objects of the brain (e.g. tracts, hubs, or parcellations of the brain). Such visual representations can reveal internal structures hidden by the skin and bones, and can be used to diagnose and treat various different diseases.

The medical professional can use the selectable options 306 to specify particular actions (e.g. by making selections in the GUI 300 presented at the user device 104) that the medical professional would like to take with regards to the processed data 302. The medical professional can also choose options to export the processed data within an IT network of the hospital or other medical setting where the medical professional works. The medical professional can save the exported data (e.g., in the data store 108 in FIG. 1), which can be used in future research and analysis.

The GUI 300 presents only some options that may be presented to the medical professional with regards to the processed data 302. One or more other options are also possible and can be presented in the GUI 300 and/or in additional GUIs that are outputted at the user device 104.

Moreover, as described herein, the GUI 300 can be part of a specialized computing system in the hospital IT infrastructure. Sometimes, the GUI 300 can also be accessible via a web browser. The GUI 300 may be configured—e.g. by authentication mechanisms such as login using username and/or password, biometric detection, and/or the like—to be used by only authorized individuals, such as clinicians (e.g. doctors, nurses, clinical staff, or the like), other medical professionals, or other authorized users (e.g. network administrator, technical staff, or the like) at the hospital or other medical setting. In some implementations, the GUI 300 can also be in communication with or otherwise linked to one or more external devices, such as remote computers, that can be used to facilitate brain surgery or other medical procedures.

Although a brain image is useful for a medical professional, the medical professional can benefit more if they have additional information about components of the brain that is imaged. This additional information can be advantageous for the medical professional to make more informed decisions with regard to diagnosis, treatment, and medical procedures. Accordingly, as shown in FIG. 3, the GUI 300 can provide the medical professional with tools (e.g., such as the selectable options 306) that allow the medical professional to interact with the modelled version of the particular brain. The medical professional can provide input for selecting portions of the processed data 302. The selected portions can be objects—e.g. brain tracts and/or brain parcellations—that the medical professional desires to see more information about, remove from the brain in a simulated procedure, or otherwise review and analyze. Accordingly, the medical professional can specify particular portions of the brain to analyze. The medical professional may also desire to identify and specify, on the GUI 300, particular objects on several features, such as local properties of brain tissue, long-range connectivity patterns, structural markers, functional markers, and/or the like. The disclosed technology therefore can provide the medical professional with a more comprehensive, interactive, and user friendly interface for making determinations about a particular patient's brain condition(s).

Figure 4A:
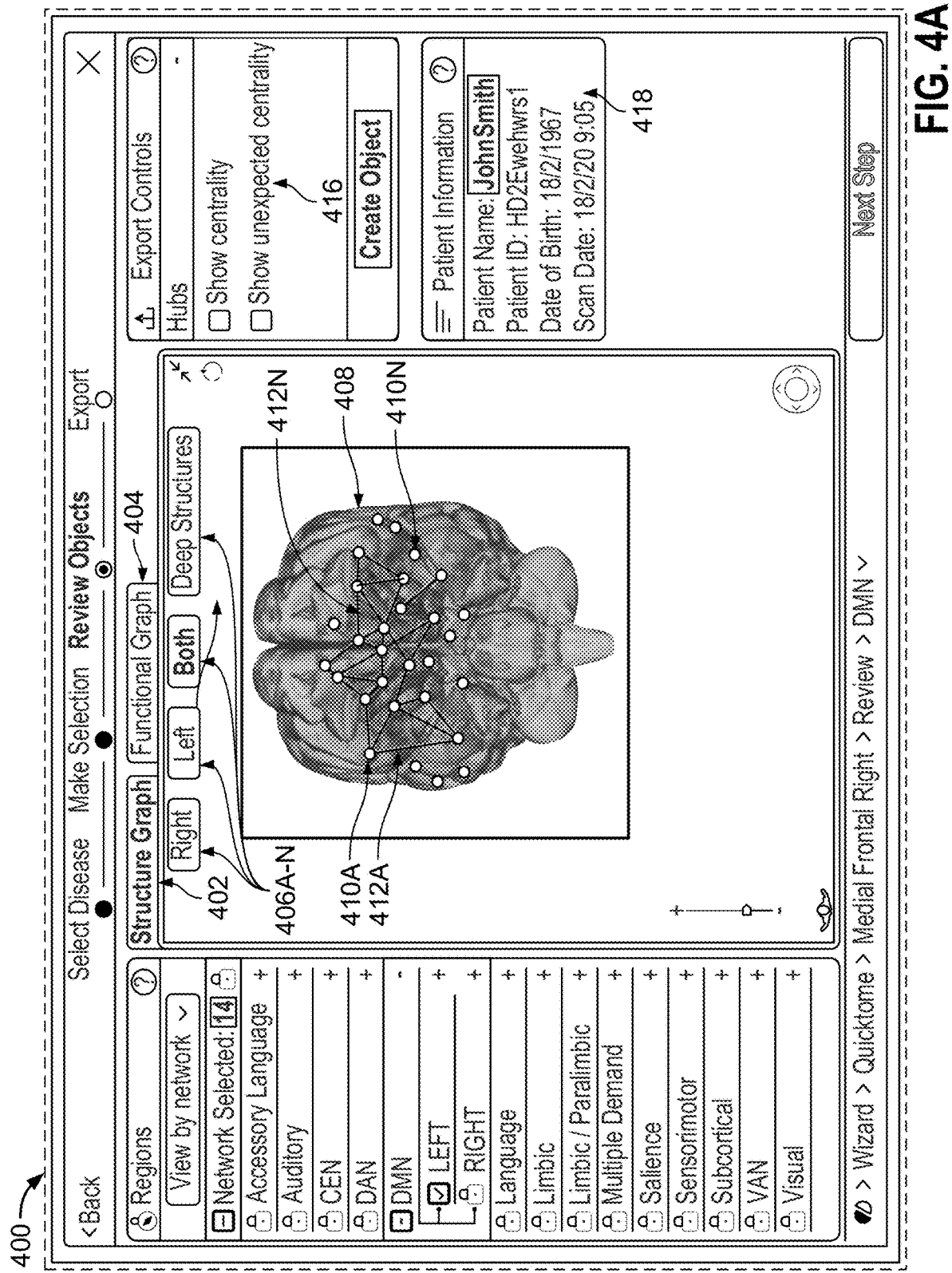
FIGS. 4A-C depict example GUI displays of the particular brain with connectivity data.
Figure 4B:
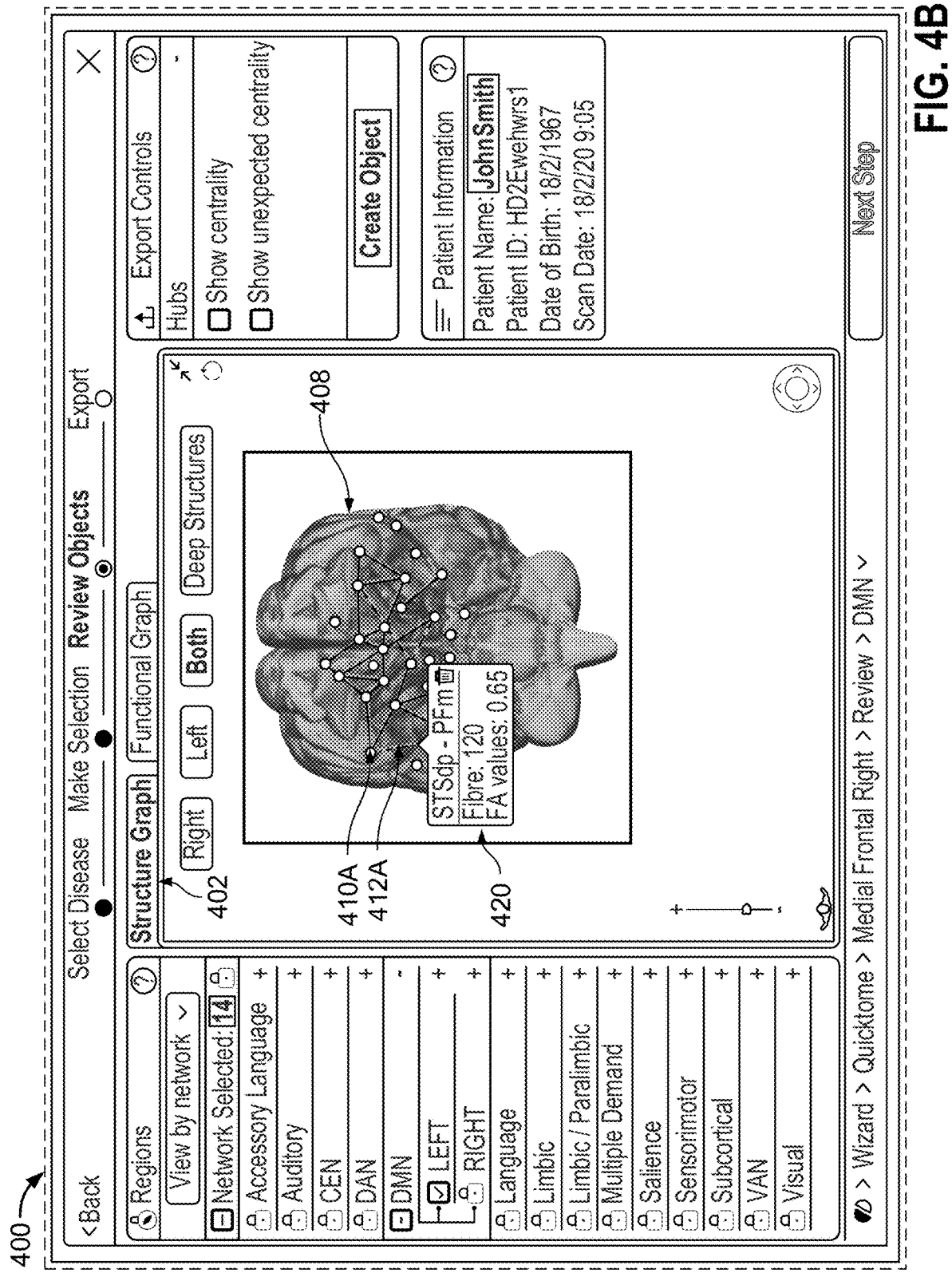
Figure 4C:
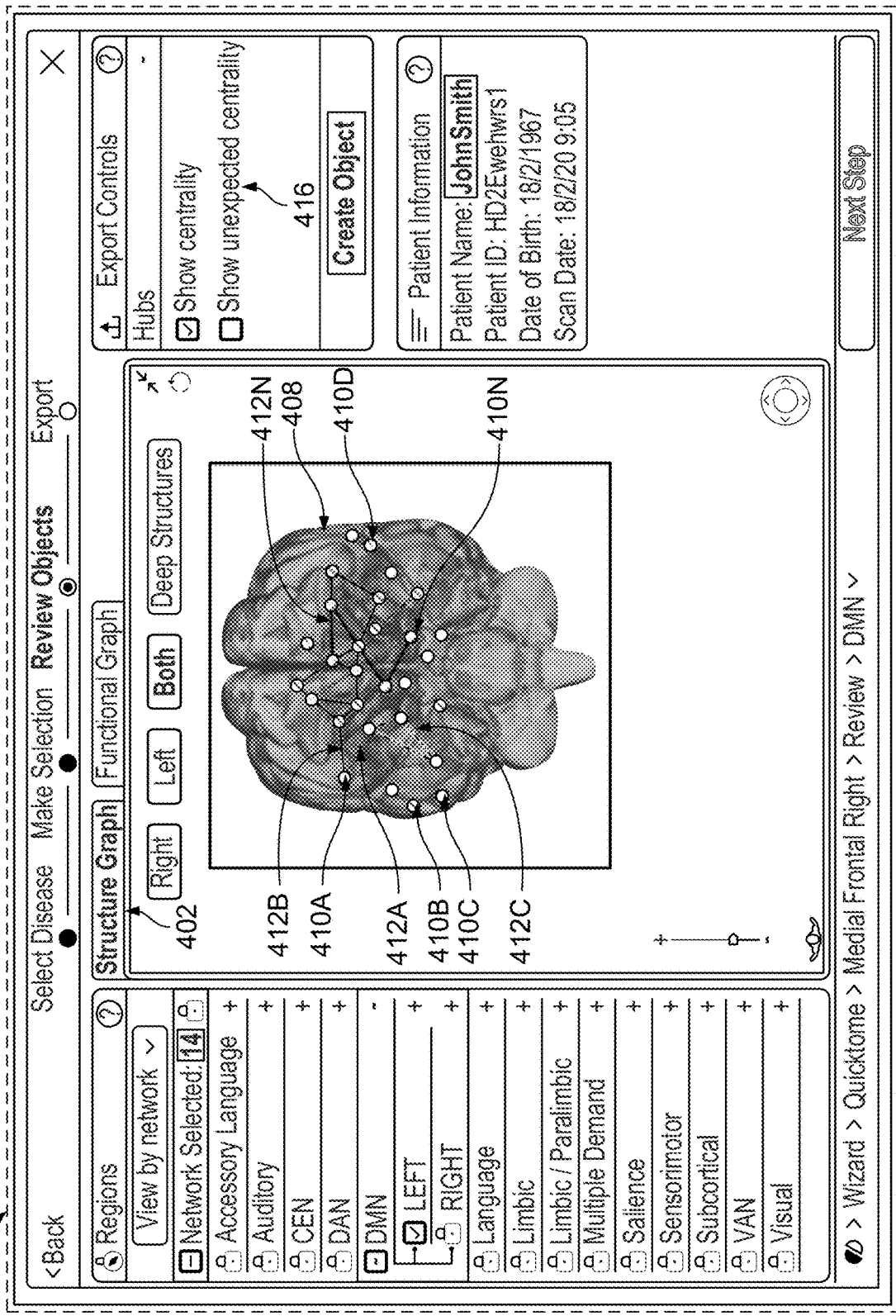

FIGS. 4A-C depict example GUI displays of the particular brain with connectivity data. Referring to FIG. 4A, GUI 400 is presented at a user device (e.g., the user device 104 in FIGS. 1-2) for display to the medical professional or other relevant user. The GUI 400 includes several selectable options, panels, and/or windows that can be customized by the medical professional and used by the medical professional to customize their interaction with and analysis of the particular brain. The GUI 400 can be used in a clinical setting (e.g., during diagnosis and treatment of a particular patient) and/or in a research setting (e.g., during population analysis/studies).

The GUI 400 can have selectable options for a structure graph 402 and a functional graph 404. In FIG. 4A, the structure graph 402 has been selected. As a result, a patient's brain can overlay a glass brain 408 (e.g., a generic representation of a brain). In other words, connectivity data associated with the particular patient's brain can be mapped onto the glass brain 408. A structural graph depicts connectivity data as a number of tracts (e.g., fibres) that have been mapped between nodes. In some implementations, different types of brain graphs or representations of a brain can be used (e.g., 2D representation of the brain, 3D representation of the brain, etc.). The functional graph 404, although not depicted, can demonstrate a connectivity matrix of the particular patient's brain in a graph, thereby demonstrating correlations between different parcellations, hubs, or portions of the brain. A functional graph depicts connectivity data as a correlation of activity of bold signals. The medical professional may choose to review one or both of the structure graph 402 and the functional graph 404 depending on a medical context and/or diagnostic condition of the particular patient.

The GUI 400 can also present the medical professional with selectable options 406A-N to view different portions of the particular patient's brain on the glass brain 408. The options 406A-N include viewing a right side of the brain, a left side of the brain, both sides of the brain, and deep structures of the brain. By selecting one of the options, the GUI 400 can be updated to reflect just the portion of the brain that has been selected. Sometimes, the GUI 400 can be updated to reflect the portion of the brain that has been selected in a first indicia and portions of the brain that were not selected in a second indicia. The first indicia, for example, can be a brighter setting (e.g., brightest setting(s)) or opacity (e.g., 100% opacity). The second indicia, for example, can be a darker setting (e.g., greyed out) or lower opacity (e.g., less than 50% opacity).

In FIG. 4A, the medical professional has selected the option to view both sides of the brain. Thus, the entire glass brain 408 is depicted with connectivity data of the particular patient's brain overlaid thereon. Nodes 410A-N are depicted on top of the glass brain 408. These nodes 410A-N are specific to the particular patient. All of the nodes 410A-N in the patient's brain can be overlaid on the glass brain 408. Sometimes, only some or a portion of the nodes 410A-N in the particular patient's brain can be overlaid on the glass brain 408. Moreover, the medical professional can optionally select which of the nodes 410A-N to overlay on the glass brain 408 and output in the GUI 400.

The nodes 410A-N are connected via edges 412A-N, which represent fibers in the particular patient's brain. As shown in the GUI 400 of FIG. 4A, some of the nodes 410A-N, such as the node 410A, are connected by the edges 412A-N to other nodes. Other nodes, such as node 410N, may not be connected to other nodes by edges 412A-N. Nodes that are connected by edges can have higher connectivity (e.g., centrality) than nodes that are not connected to other nodes by edges. Moreover, nodes that are connected to many other nodes can have higher connectivity than nodes that are connected to fewer nodes.

As shown in FIG. 4A, the nodes 410A-N can be depicted in one or more particular indicia (e.g., circles, a first color) and the edges 412A-N can be depicted in one or more other particular indicia (e.g., circles, a second color). Different indicia can be used to more clearly indicate to the medical professional what they are viewing. The different indicia can therefore improve ease of use and interaction with the GUI 400 for the medical professional.

Although the glass brain 408 is shown from one perspective in the GUI 400, the medical professional can also manually change the perspective of the brain. For example, the medical professional can zoom in and out on the glass brain 408 (e.g., by scrolling with a mouse, selecting zoom buttons or other options that are presented in the GUI 400, etc.). Zooming in and out can change what nodes and/or edges are displayed and/or how such nodes and/or edges are displayed. The medical professional can also rotate a desired amount around the glass brain 408 (e.g., by clicking with a mouse on the GUI 400 and dragging the cursor left, right, up, and down, selecting rotation buttons or other options that are presented in the GUI 400, etc.). This provides for improved user functionality, thereby making it easier, more intuitive, and seamless for the medical professional to view different portions of the patient's brain and to further analyze connectivity data associated with different portions (e.g., hubs, parcellations) of the particular patient's brain.

Moreover, whenever the medical professional selects one or more of the nodes 410A-N and/or the edges 412A-N to be removed, the computer system can automatically re-compute the connectivity matrix for the particular patient. The re-computed matrix can be automatically presented in the GUI 400 on the glass brain 408. The medical professional may not have to navigate different GUIs or select options to have the connectivity matrix re-computed and loaded on the glass brain 408. Therefore, the connectivity matrix can be updated in real-time to provide a more seamless user experience for the medical professional.

The GUI 400 can also include an object creation panel 416 and patient information panel 418. The object creation panel 416 can present the medical professional with one or more export controls that allow the medical professional to determine what information or views of the particular patient's brain to create. For example, the medical professional can choose to create an object that shows centrality amongst the hubs in the patient's brain. The medical professional can also choose to create an object that shows unexpected centrality amongst the hubs in the patient's brain. Creating the object can include overlaying particular nodes on the glass brain 408 and exporting this object to be stored (e.g., in the data store 108) and used for future/further analysis. For example, when the medical professional selects the option to show centrality amongst the hubs then selects the "create object" button, the computer system can load the glass brain 408 with overlaid nodes of the hubs. When the medical professional selects the option to show unexpected centrality then selects the "create object" button, the computer system can load the glass brain 408 with overlaid nodes of unexpected centrality. In some implementations, the computer system can initially load the glass brain 408 with nodes that show centrality and unexpected centrality. One or more other default configurations can also be provided in the GUI 400 upon restart or start of the brain navigation system described herein.

The patient information panel 418 can include information that is associated with the particular patient. Sometimes, image data that is used to determine and overlay nodes of the particular patient's brain can include patient identifying information. The patient identifying information can be processed out of the image data by the computer system 106 (e.g., refer to FIG. 2). Some or all of the patient identifying information can be presented in the patient information panel 418. As an example, the panel 418 can include information such as the patient's name, a patient ID, date of birth, and information about the scan or other brain image data (e.g., date of scan, ID of the scan, location where the scan was taken, etc.). Other information can also be presented in the panel 418 that may be related to the particular patient's medical visit and/or medical history/records (e.g., medications that the patient is taking, allergies of the patient, etc.). In some implementations, for example where the patient brain data is used for medical research purposes, patient information may not be presented in the GUI 400 in order to preserve patient privacy.

The GUI 400 can provide additional functionality to the medical professional. For example, the GUI 400 can provide options for the medical professional to select image data of a particular patient and/or a particular disease. The medical professional can therefore select what image data the medical professional would like mapped on the glass brain 408. The GUI 400 can also present options to the medical professional to select nodes and/or edges overlaid on the glass brain 408, review their selection(s), and then export results of such selection(s). One or more other options can be provided to the medical professional with regards to selecting regions of the patient's brain, network selection, accessory language, auditory, CEN, DAN, DMN, language, limbic, limbic/paralimbic, multiple demand, salience, sensorimotor, subcortical, VAN, and visual. One or more of the abovementioned options can also be locked (e.g., represented by a lock icon), which means that the medical professional may not configure such options in some scenarios. A plus icon near any of the abovementioned options can provide the user with functionality to expand the functional network into functional sub-networks. One or more other user-selectable options can be provided in the GUI 400 to improve or otherwise expand user functionality.

FIG. 4B depicts updated GUI 400 based on received user input. The medical professional can provide input such as hovering over one or more of the nodes 410A-N and/or the edges 412A-N. In the example of FIG. 4B, the medical professional has hovered their mouse over the edge 412A. In response to receiving this user input, the computer system displays information 420 about the edge 412A. The information 420 is depicted as overlaying a portion of the GUI 400. Thus, when the medical professional hovers their mouse over the edge 412A, the GUI 400 can automatically and seamlessly be updated to include the information 420. This provides for a user-friendly interface that does not require the medical professional to navigate between different windows or GUIs. This makes it easier and faster for the medical professional to analyze information about the particular patient's brain and make decisions (e.g., regarding diagnosis, treatment, medical procedures, and/or other research or analysis) based on that information.

The information 420 can include a name of the edge 412A, values of the edge 412A, weights, and other information associated with the edge 412A. The information 420 can also include a selectable option to remove the edge 412A (e.g., represented by a trashcan icon). The values and weights of the edge 412A can include a number of tract (e.g., fibre) connections and/or a functional correlation value. The information 420 can also include, but is not limited to, other tract values (e.g., length), graph metrics associated with edge values, and/or diffusion measures. The diffusion measures can include fractional anisotropy (FA), apparent diffusion coefficient (ADC), mean diffusivity (MD), axial diffusivity (AD), and/or radial diffusivity (RD). Moreover, when the medical professional hovers over the edge 412A, the edge 412A can be illuminated, highlighted, or otherwise depicted in a different indicia in order to emphasize which edge the medical professional is focusing on. This can be advantageous to make the GUI 400 more user-friendly.

FIG. 4C depicts updated GUI 400 based on receiving user input indicating selection of centrality amongst hubs in the create object panel 416. As described above, when user input is received, the computer system can automatically update the GUI 400 to provide a seamless transition of information that is presented to the medical professional. This can be beneficial to make the GUI 400 more intuitive and user-friendly.

Here, because the medical professional has selected the option to view centrality of the hubs in the particular patient's brain, the GUI 400 has been updated to show centrality (e.g., connectivity) amongst the nodes 410A-N on the glass brain 408. The nodes 410A-N and the edges 412A-N are presented in different indicia to visually depict the different levels of centrality. The indicia can be colors, as shown in FIG. 4C. One or more other indicia can also be used, such as patterns, dotted lines, different shapes, and/or shading.

Nodes that are red (e.g., a first indicia) have higher centrality than nodes that are blue (e.g., a second indicia). Higher centrality means that the corresponding node or nodes has many connections to other nodes, where those connections are also strong. Moreover, different gradients of colors can be used to demonstrate different degrees of centrality. For example, a node that is dark red can have the highest centrality in comparison to a node that is light red. A node that is dark blue can have the lowest centrality in comparison to a node that is light blue. The medical professional can view the different colored nodes to more quickly and easily determine which nodes can be removed during a medical procedure and/or how removal of such nodes would impact other nodes, edges, parcellations, and/or hubs of the particular patient's brain. Although red and blue colors are use and depicted in FIG. 4C, different indicia (e.g., colors, patterns, shading, shapes, etc.) can also be used to demonstrate differences in centrality amongst the nodes 410A-N.

In FIG. 4C, nodes such as 410A are light red, indicating centrality that is not the highest centrality but is higher than a threshold level that indicates low centrality. Some of the nodes, such as 410A, can also have an edge, such as edge 412A. Edges such as the edge 412A can connect the node 410A with one or more other nodes 410B-N. In some implementations, one or more of the nodes 410A-N may not be connected to other nodes.

Nodes such as 410B are dark blue, indicating the lowest centrality amongst the nodes 410A-N. Some of these dark blue nodes can be connected to other nodes (e.g., via edges such as edge 412B). Moreover, some of the dark blue nodes (e.g., or nodes in an indicia representing the lowest centrality amongst the nodes) may not be connected to any other nodes. Removing any one of the lowest centrality nodes that are not connected to others may not impact the network of nodes in the particular patient's brain.

Nodes such as node 410C are light blue, indicating a centrality that is lower than the threshold level but not the lowest centrality. Some of these light blue nodes can be connected to other nodes (e.g., via edges such as edge 412C). Some of these nodes also may not be connected to other nodes, in some implementations.

Nodes such as node 410D are pink, which indicates higher than normal centrality, more like a hub. Some of these pink nodes can be connected to other nodes that are represented in same or different indicia. Some of these nodes also may not be connected to other nodes.

Nodes such as node 410N are dark red, indicating the highest centrality amongst the nodes 410A-N. Some of these dark red nodes can be connected to other nodes (e.g., via edges such as edge 412N). Some of these nodes also may not be connected to other nodes.

One or more other indicia can be used to represent different centrality amongst the hubs in the patient's brain, as described herein. Moreover, centrality can be expressed in one or more ranges of values. For example, highest centrality (e.g., a red color or other indicia) can be represented by a number of connections between nodes that is greater than a first threshold level but less than or equal to a second threshold level. Medium centrality (e.g., a pink color or other indicia) can be represented by a number of connections between nodes that is less than the first threshold but greater than a third threshold level, where the third threshold level is less than both the first and second threshold levels. Lowest centrality (e.g., dark blue or other indicia) can be represented by a number of connections between nodes that is less than the third threshold level but greater than or equal to a fourth threshold level, where the fourth threshold level is less than the first, second, and third threshold levels. In some implementations, the fourth threshold level can be 0, which means that a particular node has no connections. In yet some implementations, the lowest centrality can be represented by 0 connections between nodes. One or more other ranges of centrality can be defined and then displayed on the glass brain 408.

Figure 5A:
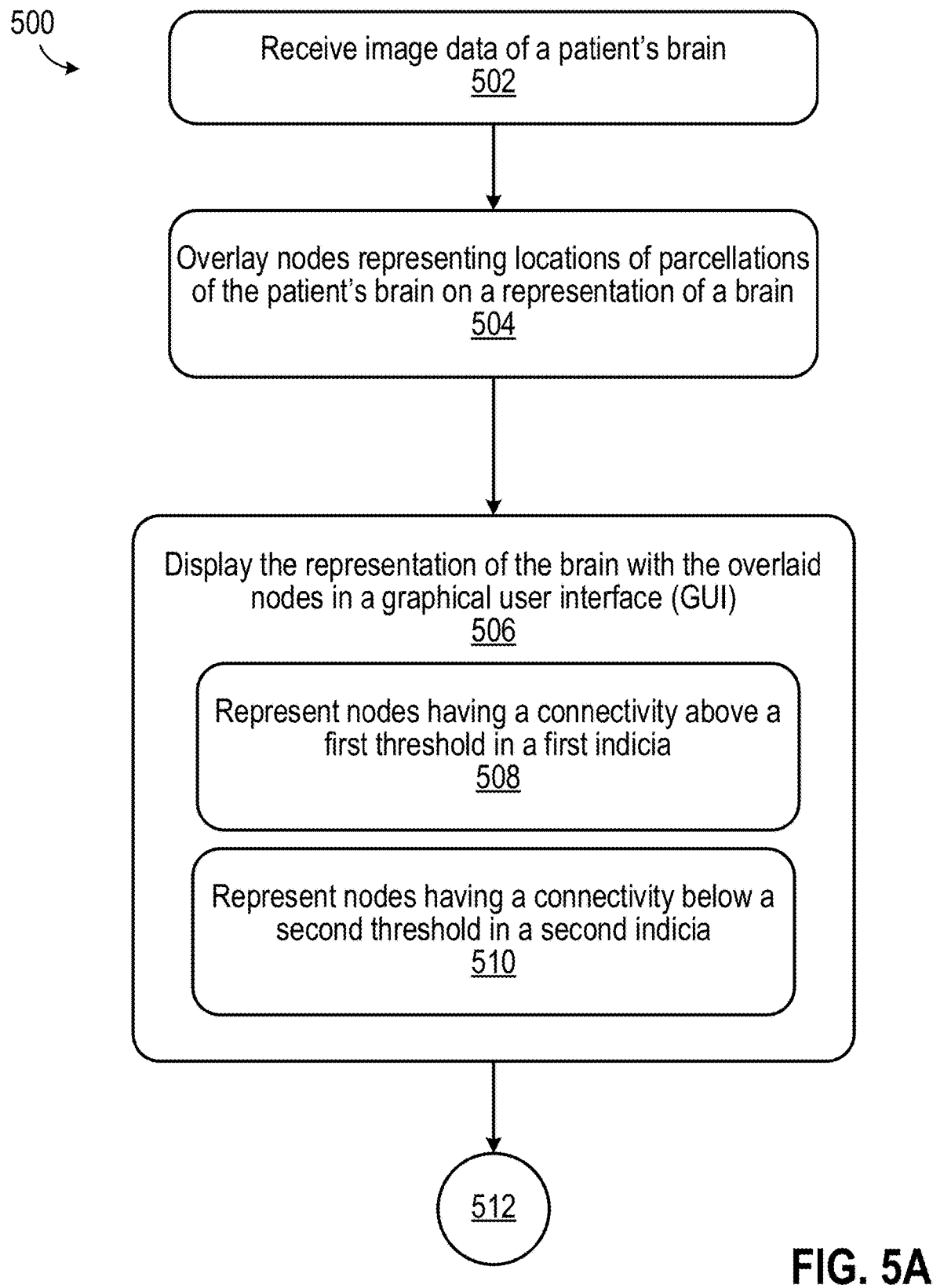
FIGS. 5A-B is a flowchart of a process for generating GUI displays of the particular brain with connectivity data.
Figure 5B:
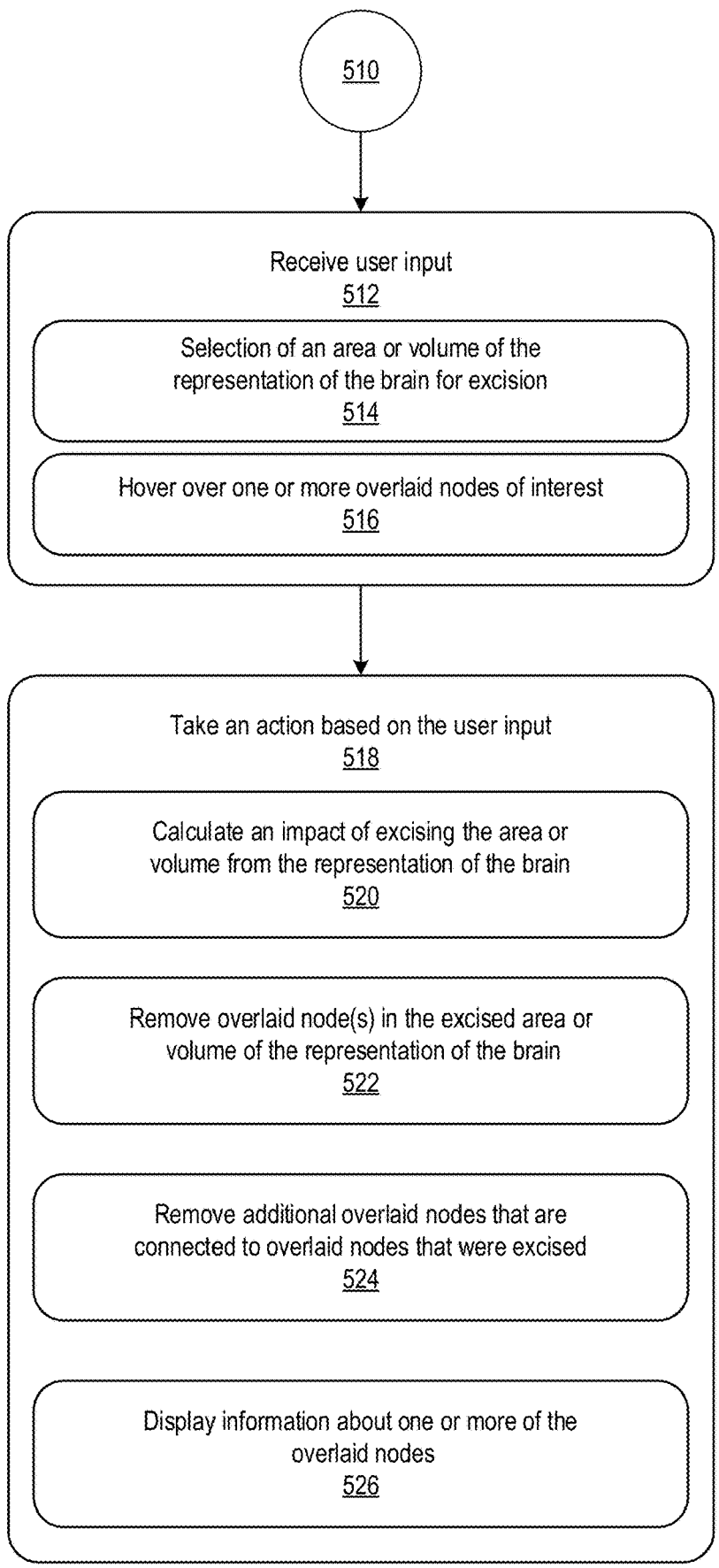

FIGS. 5A-B is a flowchart of a process 500 for generating GUI displays of the particular brain with connectivity data. The process 500 can be performed by the computer system 106 (e.g., refer to FIGS. 1-2). Sometimes, the process 500 can be performed by the user device 104. In yet some implementations, the process 500 can be performed by another computer system, computer, device, server, network of devices, network of computers, or combination thereof. For illustrative purposes, the process 500 is described from a perspective of a computer system.

Referring to the process 500 in both FIGS. 5A-B, the computer system can receive image data of a patient's brain in 502. The image data can be received from a medical imaging device (e.g., the medical imaging device 110 in FIGS. 1-2). The image data can also be received from a user device (e.g., the user device 104 in FIGS. 1-2). Sometimes, the computer system can retrieve, from a data store (e.g., the data store 108 in FIGS. 1-2), image data of the patient's brain. The image data can include parcellations of the patient's brain that have been annotated and labeled. One or more of the parcellations of the patient's brain can include hubs. The parcellations can be manually annotated and labeled by a medical professional (e.g., clinician). The parcellations can also be automatically annotated and labeled by a computer system (e.g., the computer system 106) using one or more machine learning trained models, algorithms, techniques, and/or processes. The image data can include other/additional information about the patient, such as their name, a patient ID, a date of birth, a date that the image data was captured/recorded, and/or other relevant medical information (e.g., refer to FIGS. 3-4). As described herein, the other information can be presented in a GUI at the user device in a panel, pop out window, or other portion of the GUI so as to not interfere or overlap with a representation of the patient's brain.

In 504, the computer system can overlay nodes representing locations of parcellations of the patient's brain on a representation of a brain. Overlaying the nodes can include connecting high connectivity nodes and low connectivity nodes by edges. The edges can represent fibers in the patient's brain. The representation of the brain can be a glass brain (e.g., refer to FIGS. 3-4). The same glass brain can be used for all patient brains. One or more other types of representations of the brain can be used to visually depict centrality/connectivity data for different patient brains.

Next, the computer system can display the representation of the brain with the overlaid nodes in a GUI (506). Sometimes, the computer system can also display a graph with edges of correlation. The computer system can represent nodes having a connectivity above a first threshold in a first indicia (508). The first indicia can be a first color (e.g., red). Nodes in the first indicia can have high centrality. The computer system can also represent nodes having a connectivity below a second threshold in a second indicia (510). The second indicia can be a second color (e.g., blue). Nodes in the second indicia can have low centrality. One or more other indicias can be used to represent centrality/connectivity of each of the nodes that are depicted on the representation of the brain.

Sometimes, each of the nodes can be represented in different shades of colors to depict varying levels of centrality between the highest and lowest centrality. For example, nodes having the highest centrality can be depicted in bright red. Nodes with slightly lower centrality can be depicted in shades of red that are darker than the bright red. The nodes can then transition to a different color to demonstrate centrality that is below some threshold. For example, nodes with the lowest centrality can be depicted in bright blue. Nodes that have centrality below the threshold but not the lowest centrality can be depicted in darker shades of blue that transition to the bright blue when the nodes have the lowest centrality. Sometimes, multiple different colors (e.g., more than 2 colors) can be used to depict different threshold levels of centrality. Other shades or indicia can be used to visually depict the different levels of centrality amongst the nodes and their connecting edges.

The connectivity of the nodes can be a number of connections between the nodes. Thus, the more connections between nodes, the higher connectivity (e.g., the more centrality). The fewer connections between nodes, the lower connectivity (e.g., the less centrality). During a surgery or other procedure, removing nodes that have high connectivity can have a more significant impact on other parcellations or hubs of the brain and/or cognitive abilities of a particular patient. Thus, the disclosed technology provides for a more intuitive and user-friendly display of interconnectivity amongst nodes for the particular patient's brain in order to assist a medical professional in assessing the patient's brain and making decisions about how to proceed with diagnosis, treatment, and/or surgery for the particular patient. Sometimes, the connectivity of the nodes can also be a correlation of activity of bold signals of the brain. The connectivity of the nodes can also be a number of connections between the nodes and a correlation of activity in bold signals.

The connectivity of the nodes can be based on a variety of factors. For example, the connectivity of the nodes can be based at least in part on a plurality of diffusion tensor imaging (DTI) data and/or diffusion weighted imaging (DWI) data. This data can indicate tracks that connect to parcellations of the patient's brain. As another example, the connectivity of the nodes can be based at least in part on blood oxygen consumption of the parcellations of the patient's brain.

The computer system can receive user input in 512. The user input can include selection of an area or volume of the representation of the brain for excision (514). The user input can also include hovering over one or more of the overlaid nodes of interest (516). The user input can be made by the medical professional at the user device (e.g., the user device 104 in FIGS. 1-2). The medical professional can provide the user input in order to glean more information about a particular parcellation, hub, node, and/or connection between nodes in the particular patient's brain. As an example, the medical professional can click on one or more nodes that the medical professional would consider removing during an actual surgical procedure for that patient. The medical professional can also highlight one or more nodes with high or low graph measures (e.g., centrality, participation, modularity measures, etc.). As another example, the medical professional can click on one or more parcellations or hubs that the medical professional would consider removing, puncturing, slicing into, or otherwise touching during an actual surgical procedure. As yet another example, the medical professional can select (e.g., drag over a portion of the representation of the brain or use a tool in the GUI to draw an area around a portion of the representation of the brain) an area that includes one or more parcellations, hubs, and/or nodes in the brain that the medical professional would consider removing during an actual surgical procedure. As another example, the medical professional can hover their mouse or cursor over a particular parcellation, hub, node, and/or edge in order to view additional information about that portion of interest in the patient's brain.

Based on the user input, the computer system can take some action on the representation of the brain in 518. For example, the computer system can calculate an impact of excising the area or volume from the representation of the brain (520). Sometimes, the impact of excising the selected area or volume of the brain can include interference(s) on cognitive functionality of the patient's brain. The computer system can generate output indicating whether the particular patient would be impaired by removal of the user-selected portion of the brain.

The output can be presented to the medical professional as text. The text can indicate what type of cognitive impairment is likely for the particular patient. The text can overlay a portion of the GUI and/or the representation of the brain. The text can also be presented in a separate interface, window, or pop out window. Sometimes, the output can be presented to the medical professional as a visual modification of the representation of the brain. In other words, if the user-selected portion of the brain is removed but nodes in that portion of the brain connect to nodes in other portions of the brain, then the computer system can update the representation of the brain to show connected edges, nodes, hubs, and/or parcellations of the brain also being cut or otherwise affected. The computer system can, for example, change a color or other indicia of the connected edges, nodes, hubs, and/or parcellations of the brain to demonstrate that such connected portions of the brain would also be affected by removal of the user-selected portion of the brain.

The computer system can also remove overlaid nodes in the excised area or volume of the representation of the brain (522). For example, the representation of the brain can be updated to show connectivity amongst nodes once the nodes in the user-selected portion of the brain are removed. Sometimes, the computer system can remove additional overlaid nodes that are connected to the overlaid nodes that were excised in 520 (524) (e.g., where the additional overlaid nodes would be impacted by removal of the nodes in the excised portion). As mentioned above, the computer system can remove nodes in the excised portion of the brain as well as nodes that may be connected to the removed nodes. This can provide a visual representation of an effect that removing the user-selected portion of the brain would have on the rest of the patient's brain. Moreover, the computer system can update or otherwise change an indicia for nodes that remain in the brain (e.g., nodes that are not removed and are not connected to the nodes that are removed from the user-selected portion of the brain). For example, connectivity of nodes that are not removed can change based on nodes that are removed in 522. How this connectivity changes is dependent on how connectivity is defined. As an illustrative example, in terms of number of connections, when nodes are removed, nodes that remain can have a reduced number of neighboring nodes. The reduced number of neighboring nodes means that the remaining nodes have fewer connections.

Another action can include displaying additional information about one or more of the overlaid nodes in 526. When the medical professional hovers over the one or more nodes, the computer system can present information about the one or more nodes to the medical professional. This information can be displayed over a portion of the GUI. Sometimes, this information can be displayed in a separate window, a pop-out panel, or another GUI. The information can indicate connectivity data, centrality data, name of the node, weight of the node, and other information about the node, parcellation, hub, and/or edges that can be used by the medical professional to make informed decisions for diagnosis, treatment, procedures, and other medical research or analysis.

As yet another example, the computer system can load, in atlas form, one or more nodes or edges that are selected or clicked on by the medical professional. Thus, the selected nodes or edges can be loaded in another window or GUI with the corresponding parcellation or parcellation/track combination. One or more other actions are also possible and can be taken by the computer system in response to receiving the user input in 518, such as communicating and interfacing with other connectomic interfaces.

Figure 6:
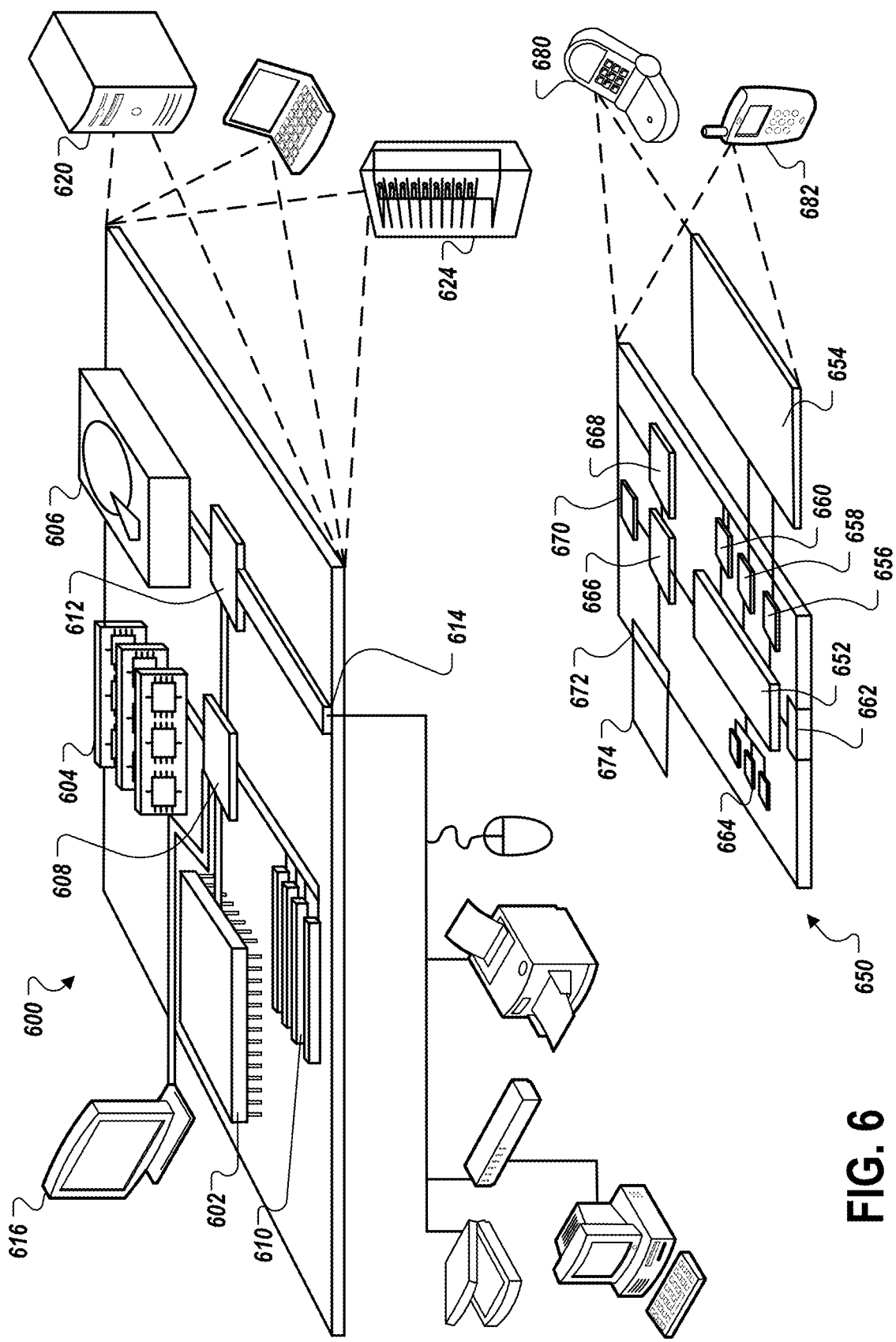
FIG. 6 is a schematic diagram that shows an example of a computing device and a mobile computing device.

FIG. 6 shows an example of a computing device 600 and an example of a mobile computing device that can be used to implement the techniques described here. The computing device 600 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and can be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 604 stores information within the computing device 600. In some implementations, the memory 604 is a volatile memory unit or units. In some implementations, the memory 604 is a non-volatile memory unit or units. The memory 604 can also be another form of computer-readable medium, such as a magnetic or optical disk.

The storage device 606 is capable of providing mass storage for the computing device 600. In some implementations, the storage device 606 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 604, the storage device 606, or memory on the processor 602.

The high-speed interface 608 manages bandwidth-intensive operations for the computing device 600, while the low-speed interface 612 manages lower bandwidth-intensive operations. Such allocation of functions is exemplary only. In some implementations, the high-speed interface 608 is coupled to the memory 604, the display 616 (e.g., through a graphics processor or accelerator), and to the high-speed expansion ports 610, which can accept various expansion cards (not shown). In the implementation, the low-speed interface 612 is coupled to the storage device 606 and the low-speed expansion port 614. The low-speed expansion port 614, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 600 can be implemented in a number of different forms, as shown in the figure. For example, it can be implemented as a standard server 620, or multiple times in a group of such servers. In addition, it can be implemented in a personal computer such as a laptop computer 622. It can also be implemented as part of a rack server system 624. Alternatively, components from the computing device 600 can be combined with other components in a mobile device (not shown), such as a mobile computing device 650. Each of such devices can contain one or more of the computing device 600 and the mobile computing device 650, and an entire system can be made up of multiple computing devices communicating with each other.

The mobile computing device 650 includes a processor 652, a memory 664, an input/output device such as a display 654, a communication interface 666, and a transceiver 668, among other components. The mobile computing device 650 can also be provided with a storage device, such as a micro-drive or other device, to provide additional storage. Each of the processor 652, the memory 664, the display 654, the communication interface 666, and the transceiver 668, are interconnected using various buses, and several of the components can be mounted on a common motherboard or in other manners as appropriate.

The processor 652 can execute instructions within the mobile computing device 650, including instructions stored in the memory 664. The processor 652 can be implemented as a chipset of chips that include separate and multiple analog and digital processors. The processor 652 can provide, for example, for coordination of the other components of the mobile computing device 650, such as control of user interfaces, applications run by the mobile computing device 650, and wireless communication by the mobile computing device 650.

The processor 652 can communicate with a user through a control interface 658 and a display interface 656 coupled to the display 654. The display 654 can be, for example, a TFT (Thin-Film-Transistor Liquid Crystal Display) display or an OLED (Organic Light Emitting Diode) display, or other appropriate display technology. The display interface 656 can comprise appropriate circuitry for driving the display 654 to present graphical and other information to a user. The control interface 658 can receive commands from a user and convert them for submission to the processor 652. In addition, an external interface 662 can provide communication with the processor 652, so as to enable near area communication of the mobile computing device 650 with other devices. The external interface 662 can provide, for example, for wired communication in some implementations, or for wireless communication in other implementations, and multiple interfaces can also be used.

The memory 664 stores information within the mobile computing device 650. The memory 664 can be implemented as one or more of a computer-readable medium or media, a volatile memory unit or units, or a non-volatile memory unit or units. An expansion memory 674 can also be provided and connected to the mobile computing device 650 through an expansion interface 672, which can include, for example, a SIMM (Single In Line Memory Module) card interface. The expansion memory 674 can provide extra storage space for the mobile computing device 650, or can also store applications or other information for the mobile computing device 650. Specifically, the expansion memory 674 can include instructions to carry out or supplement the processes described above, and can include secure information also. Thus, for example, the expansion memory 674 can be provide as a security module for the mobile computing device 650, and can be programmed with instructions that permit secure use of the mobile computing device 650. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 664, the expansion memory 674, or memory on the processor 652. In some implementations, the computer program product can be received in a propagated signal, for example, over the transceiver 668 or the external interface 662.

The mobile computing device 650 can communicate wirelessly through the communication interface 666, which can include digital signal processing circuitry where necessary. The communication interface 666 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 668 using a radio-frequency. In addition, short-range communication can occur, such as using a Bluetooth, WiFi, or other such transceiver (not shown). In addition, a GPS (Global Positioning System) receiver module 670 can provide additional navigation- and location-related wireless data to the mobile computing device 650, which can be used as appropriate by applications running on the mobile computing device 650.

The mobile computing device 650 can also communicate audibly using an audio codec 660, which can receive spoken information from a user and convert it to usable digital information. The audio codec 660 can likewise generate audible sound for a user, such as through a speaker, e.g., in a handset of the mobile computing device 650. Such sound can include sound from voice telephone calls, can include recorded sound (e.g., voice messages, music files, etc.) and can also include sound generated by applications operating on the mobile computing device 650.

The mobile computing device 650 can be implemented in a number of different forms, as shown in the figure. For example, it can be implemented as a cellular telephone 680. It can also be implemented as part of a smart-phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other. In some implementations, the computing system can be cloud based and/or centrally processing data. In such case anonymous input and output data can be stored for further analysis. In a cloud based and/or processing center set-up, compared to distributed processing, it can be easier to ensure data quality, and accomplish maintenance and updates to the calculation engine, compliance to data privacy regulations and/or troubleshooting.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A method comprising:
receiving image data of a patient's brain;
processing the image data to map the image data of the patient's brain to a 3D representation of a brain that is user-interactive for purposes of at least one of treatment, diagnosis, and analysis of a condition of the patient;
overlaying nodes representing locations of parcels of the patient's brain on the 3D representation of the brain, wherein using parcels is a mechanism that reduces complexity of analyzing at least one of electrical activity and tracts of the patient's brain by using a finite number of specified domains;
displaying the 3D representation of the brain with the overlaid nodes in a graphical user interface (GUI), wherein nodes having a connectivity above a first threshold are displayed in a first indicia and nodes having a connectivity below a second threshold are displayed in a second indicia;
receiving user input, wherein the user input includes at least hovering an indicator over one or more of the overlaid nodes in response to displaying in the GUI a) the 3D representation of the brain and, at the same time, b) the overlaid nodes overlaid on the 3D representation of the brain; and in response to the indicator hovering over the one or more of the overlaid nodes, automatically
forwarding updated information to a user device for display over a portion of the GUI, the updated information being information about the one or more of the overlaid nodes.

2. The method of claim 1, wherein the connectivity of the nodes is a number of connections between the nodes.

3. The method of claim 1, wherein the connectivity of the nodes is a correlation of activity of bold signals.

4. The method of claim 1, wherein the connectivity of the nodes is a number of connections between the nodes and a correlation of activity in bold signals.

5. The method of claim 1, wherein the connectivity of the nodes is based at least in part on blood oxygen consumption of the parcels of the patient's brain.

6. The method of claim 1, wherein the user input includes selection of an area or volume of the representation of the brain for excision during a simulated procedure.

7. The method of claim 6, wherein taking an action based on the user input comprises calculating an impact on the patient in response to excising the area or volume of the representation of the brain during the simulated procedure.

8. The method of claim 7, wherein the impact on the patient in response to excising the area or volume of the representation of the brain includes interferences on cognitive functionality of the patient's brain.

9. The method of claim 6, wherein taking an action based on the user input comprises removing one or more of the overlaid nodes in the excised area or volume of the representation of the brain during the simulated procedure.

10. The method of claim 1, wherein forwarding information to a user device comprises displaying, in a pop out window over the portion of the GUI at the user device, text indicating at least one of (i) a number of tract connections associated with the one or more of the overlaid nodes and (ii) a functional correlation value associated with the one or more of the overlaid nodes.

11. The method of claim 1, wherein one or more of the parcels of the patient's brain include hubs.

12. The method of claim 1, wherein the first indicia is a first color and the second indicia is a second color.

13. The method of claim 1, wherein the user input includes selection of one of the overlaid nodes, and taking an action based on the user input comprises displaying information about the selected one of the overlaid nodes in a second GUI.

14. The method of claim 1, further comprising connecting high connectivity nodes and low connectivity nodes by edges, wherein the edges represent fibers.

15. The method of claim 14, further comprising displaying, in the GUI, a graph with the edges of correlation.

16. The method of claim 1, wherein the nodes in the first indicia have high centrality and the nodes in the second indicia have low centrality.

17. A system comprising:
at least one programmable processor; and
a machine-readable medium storing instructions that, when executed by the at least one programmable processor, cause the at least one programmable processor to perform operations comprising:
receiving image data of a patient's brain;
processing the image data to map the image data of the patient's brain to a 3D representation of a brain that is user-interactive for purposes of at least one of treatment, diagnosis, and analysis of a condition of the patient;
overlaying nodes representing locations of parcels of the patient's brain on the 3D representation of the brain, wherein using parcels is a mechanism that reduces complexity of analyzing at least one of electrical activity and tracts of the patient's brain by using a finite number of specified domains;
displaying the 3D representation of the brain with the overlaid nodes in a graphical user interface (GUI), wherein nodes having a connectivity above a first threshold are depicted in a first indicia and nodes having a connectivity below a second threshold are depicted in a second indicia;
receiving user input, wherein the user input includes at least hovering an indicator over one or more of the overlaid nodes in response to displaying in the GUI a) the 3D representation of the brain and, at the same time, b) the overlaid nodes overlaid on the 3D representation of the brain; and in response to the indicator hovering over the one or more of the overlaid nodes, automatically
forwarding updated information to a user device for display over a portion of the GUI, the updated information being information about the one or more of the overlaid nodes.

18. The method of claim 1, wherein the information about the one or more of the overlaid nodes includes a diffusion measure associated with the one or more of the overlaid nodes, the diffusion measure being at least one of a fractional anisotropy (FA) value, an apparent diffusion coefficient (ADC), a mean diffusivity (MD) value, an axial diffusivity (AD) value, and a radial diffusivity (RD) value.

19. The method of claim 1, wherein the parcels of the patient's brain represent at least one of functional activity, cytoarchitecture, and structural connectivity, but not blood vessels.

20. A method comprising:

receiving image data of a patient's brain;

processing the image data to map the image data of the patient's brain to a representation of a brain that is user-interactive for purposes of at least one of treatment, diagnosis, and analysis of a condition of the patient;

overlaying nodes representing locations of parcels of the patient's brain on the representation of the brain, wherein using parcels is a mechanism that reduces complexity of analyzing at least one of electrical activity and tracts of the patient's brain by using a finite number of specified domains;

displaying the representation of the brain with the overlaid nodes in a graphical user interface (GUI), wherein nodes having a connectivity above a first threshold are displayed in a first indicia and nodes having a connectivity below a second threshold are displayed in a second indicia;

receiving user input, wherein the user input includes at least hovering over one or more of the overlaid nodes, and wherein the user input includes selection of an area or volume of the representation of the brain for excision during a simulated medical procedure; and taking an action based on the user input, wherein the action comprises at least forwarding information to a user device for display of information about the one or more of the overlaid nodes over a portion of the GUI, wherein taking an action based on the user input further comprises removing one or more of the overlaid nodes in the excised area or volume of the representation of the brain during the simulated procedure, and removing additional nodes of the overlaid nodes, wherein the additional nodes are connected to the one or more of the overlaid nodes that are in the excised area or volume of the representation of the brain.

* * * * *